United States Patent
Schulze zur Wiesche et al.

(10) Patent No.: US 10,137,068 B2
(45) Date of Patent: Nov. 27, 2018

(54) METHOD FOR MAINTAINING THE COLOR OF DYED AND/OR HIGHLIGHTED KERATIN FIBRES

(71) Applicant: Henkel AG & Co. KGaA, Duesseldorf (DE)

(72) Inventors: Erik Schulze zur Wiesche, Hamburg (DE); René Krohn, Norderstedt (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 16 days.

(21) Appl. No.: 15/536,697

(22) PCT Filed: Dec. 3, 2015

(86) PCT No.: PCT/EP2015/078453
§ 371 (c)(1),
(2) Date: Jun. 16, 2017

(87) PCT Pub. No.: WO2016/096449
PCT Pub. Date: Jun. 23, 2016

(65) Prior Publication Data
US 2018/0000701 A1    Jan. 4, 2018

(30) Foreign Application Priority Data
Dec. 17, 2014  (DE) .................. 10 2014 226 177

(51) Int. Cl.
*A61Q 5/04* (2006.01)
*A61K 8/23* (2006.01)
*A61K 8/898* (2006.01)
*A61Q 5/00* (2006.01)

(52) U.S. Cl.
CPC ............. *A61K 8/23* (2013.01); *A61K 8/898* (2013.01); *A61Q 5/004* (2013.01); *A61Q 5/04* (2013.01)

(58) Field of Classification Search
CPC ............ A61K 8/19; A61K 2800/262; A61K 2800/85; A61K 8/23; A61K 8/26; A61K 8/34; A61K 8/36; A61K 8/41; A61K 8/9706; A61K 8/982; A61K 8/988; A45D 7/04; A61Q 17/005; A61Q 1/10; A61Q 5/00; A61Q 5/04; A61Q 5/065
See application file for complete search history.

(56) References Cited

U.S. PATENT DOCUMENTS

| | | |
|---|---|---|
| 3,973,574 A | 8/1976 | Minagawa et al. |
| 4,906,461 A * | 3/1990 | Chambers ............... A61K 8/19 424/195.17 |
| 6,200,374 B1 * | 3/2001 | Stevens .................... A61K 8/19 106/217.7 |
| 2014/0165301 A1 * | 6/2014 | Schweinsberg ........ A61K 8/898 8/409 |

FOREIGN PATENT DOCUMENTS

| | | |
|---|---|---|
| DE | 19511568 A1 | 10/1996 |
| EP | 1676604 A1 | 7/2006 |

OTHER PUBLICATIONS

EPO, International Search Report and Written Opinion issued in International Application No. PCT/EP2015/078453, dated Mar. 16, 2016.

* cited by examiner

*Primary Examiner* — Audrea B Coniglio
(74) *Attorney, Agent, or Firm* — Lorenz & Kopf, LLP

(57) ABSTRACT

A method for the color retention of dyed keratin fibers is provided herein. The method includes i. applying a cosmetic composition to dyed keratin fibers as a pretreatment agent for keratin. The method further includes ii. subjecting the keratin fibers to a dyeing and/or brightening within a period of about 5 seconds to about 24 hours after to step i. The cosmetic composition has, based on its own weight, from about 0.01 to about 4.00% by weight of at least one alum and a pH value in the range of about 2.5 to about 5.

19 Claims, No Drawings

METHOD FOR MAINTAINING THE COLOR OF DYED AND/OR HIGHLIGHTED KERATIN FIBRES

CROSS-REFERENCE TO RELATED APPLICATION

This application is a U.S. National-Stage entry under 35 U.S.C. § 371 based on International Application No. PCT/EP2015/078453 filed Dec. 3, 2015 which was published under PCT Article 21(2) and which claims priority to Application No. 10 2014 226 177.5 filed Dec. 17, 2014, which are all hereby incorporated in their entirety by reference.

TECHNICAL FIELD

The disclosure is in the field of cosmetics and pertains to a method for the color retention of dyed keratin fibers, in which a cosmetic composition is applied as a pretreatment agent to keratin fibers before the hair dyeing and/or lightening, wherein the cosmetic composition has at least one alum and has an acidic pH Value. The disclosure further relates to an acidic pretreatment agent for hair that contains an alum and a silicone and to the use of the agent for the color retention of dyed hair.

BACKGROUND

The change in shape and color of hair is an important area of modern cosmetics. In this way, the appearance of the hair can be adapted to the current fashion trend and to the individual wishes of the individual consumer. The fashionable color design of hairstyles or the lamination of gray or white hair with fashionable or natural color shades is usually carried out by employing color-changing agents which permanently or only transiently, i.e., temporarily color the hair.

So-called oxidation coloring agents are used for permanent, intensive dyeings with corresponding fastness properties. Such coloring agents usually contain oxidation dye precursors, so-called developer components and coupler components. The developer components form the actual dyes under the influence of oxidizing agents or of atmospheric oxygen among each other or with coupling with one or more coupler components. The oxidation coloring agents are distinguished by excellent, long-lasting dyeing results.

For temporary dyeings, coloring or toning agents which contain so-called direct binders as a coloring component are usually used. These are dye molecules that are directly applied to the substrate and do not need an oxidative process to form the color. These dyes include, for example, the henna already known from antiquity for the dyeing of body and hair. In contrast to the dyeings obtainable with oxidation coloring agents, the dyeing results of temporary dyeings have a lower durability.

However, the keratin fibers dyed with the dyeing systems described above, in particular hair, have the disadvantage that they can change undesirably under external influences, for example, during or after hair cleaning.

"Unwanted change" is understood to mean the fading or bleeding, the loss of the color brilliance and the color shift of the hue of the hairs obtained by the respective dyeing. An undesirable change in the hair color usually occurs during or after the hair cleaning. The contact of the hair with water and surfactants, but also the massaging of the shampoo, the drying of the hair after the rinsing of the shampoo, or blow drying during the subsequent drying process can adversely affect the adhesion of the hair dye and can lead to an undesired color change and/or to less brilliance of the hair color. The undesirable change caused can be additionally amplified as a result of further environmental influences and/or sun effects.

EP 1676604A1 describes a method for improving the hue of hair in which the hair is first washed with a shampoo which, in addition to an anionic surfactant and a special silicone, contains at least one water-soluble salt, preferably sodium sulfate. In a second step, the hair is treated with a conditioning agent comprising a higher alcohol and a cationic surfactant in a specific weight ratio and then rinsed out.

However, the methods known in the prior art do not always lead to the desired color retention, in particular the reduction in the color shift.

BRIEF SUMMARY

A method for the color retention of dyed keratin fibers is provided herein. The method includes i. applying a cosmetic composition to dyed keratin fibers as a pretreatment agent for keratin. The method further includes ii. subjecting the keratin fibers to a dyeing and/or brightening within a period of about 5 seconds to about 24 hours after to step i. The cosmetic composition has, based on its own weight, from about 0.01 to about 4.00% by weight of at least one alum and a pH value in the range of about 2.5 to about 5.

A cosmetic agent for the pretreatment of keratin fibers before a dyeing and/or brightening is also provided herein. The cosmetic agent includes, based on its weight, from about 0.01 to about 4.00% by weight of at least one alum. The cosmetic agent further includes, based on its weight, from about 0.001 to about 5% by weight of at least one silicone. The cosmetic agent has a pH in the range from about 2.5 to about 5.00.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The present disclosure was therefore based on the object of providing a cosmetic method for the treatment of keratin fibers, which avoids the disadvantages of the prior art and at least attenuates them and which leads to an improved color retention, in particular to a reduced color shift. The method should be simple and performed quickly and the treated hair or the scalp is not stressed (in addition to the dye).

Surprisingly, it has now been found that a method in which a certain cosmetic composition is applied to the keratin fibers before the dyeing and/or lightening (or bleaching) leads to an improved color retention. The cosmetic composition has an acidic pH value and comprises at least one alum. In particular, the undesirable shift or alteration of the hair color in the direction of yellow or blue can be avoided or reduced by the method as contemplated herein. In addition, the method as contemplated herein ensures a special hair and/or scalp protection. The hair and the scalp are less affected by the dye, through which less damage occurs (roughness, split ends, hair breakage).

A first subject matter as contemplated herein is therefore a cosmetic method for the color retention of dyed keratin fibers in which i. a cosmetic composition is applied as a pretreatment agent on keratin fibers, and
ii. the keratin fibers are subjected to a dyeing and/or brightening within a period of about 5 seconds to about 24 hours after step i.,
wherein the cosmetic composition contains from about 0.01 to about 4.00% by weight of at least one alum, based on its weight, and has a pH in the range from about 2.5 to about 5.

In a preferred embodiment, the cosmetic composition is not washed off or rinsed out before process step ii. is carried out. Optionally, the keratin fibers can be dried after carrying out the treatment step i.

As contemplated herein, keratin-containing or keratin fibers are understood to be furs, wool, feathers and, in particular, human hair.

The method as contemplated herein can in principle be applied to keratin fibers which are dyed with permanent, semi-permanent or temporary dyeing systems and/or are bleached or brightened. However, temporary dyeing systems are designed to be washed out and/or faded over time, therefore the method of the present disclosure is particularly suitable for use on keratin fibers that are dyed and/or bleached with permanent or oxidative hair coloring agents.

In a first preferred embodiment, therefore, a cosmetic method as contemplated herein is preferred in which the keratin fibers in step ii. are subjected to an oxidative dye.

It has been found that the color retention achievable by the method as contemplated herein can be further intensified by various factors. These factors include above all the pH value of the cosmetic composition and the careful selection of particularly preferred alums.

In a second preferred embodiment, therefore, a method as contemplated herein is particularly preferred in which the cosmetic composition has a pH in the range from about 3.0 to about 4.9, particularly preferably from about 3.5 to about 4.8, and especially preferably from about 4.0 to about 4.7.

Pretreatment agents which are formulated in this pH range are particularly mild, highly scalp/skin compatible and give the keratin fibers, especially hair, a particular gloss.

"Alums" are understood to be preferably metal sulfate salts and/or double salts of the general formula $M^{I}M^{III}(SO_4)_2 \times 12H_2O$, in which:
$M^{I}$ is preferably an alkali metal ion, an ammonium ion or a guanidinium ion,
$M^{II}$ is preferably an aluminum, gallium, indium, titanium, vanadium, chromium, manganese, iron, cobalt or rhodium ion,
and which preferably crystallize it 12 molecules crystal water.

The alums especially preferred for the method as contemplated herein correspond to the formula $M^{I}Al(SO_4)_2 \times 12H_2O$, in which $M^{I}$ can preferably be an alkali metal ion, especially a sodium ion or a potassium ion, an ammonium ion or a guanidinium ion. $NaAl(SO_4)_2 \times 12H_2O$, $KAl(SO_4)_2 \times 12H_2O$, $NH_4Al(SO_4)_2 \times 12 H_2O$ as well as mixtures of these alums are particularly preferred for the color retention.

In a third preferred embodiment, a method as contemplated herein is characterized in that the cosmetic composition contains, in step i., an alum of the formula $M^{I}Al(SO_4)_2 \times 12 H_2O$ in which $M^{I}$ is a potassium, ammonium, and/or a guanidinium ion.

In a fourth particularly preferred embodiment, a method as contemplated herein is characterized in that the cosmetic composition om step i., based on its weight, contains from about 0.05 to about 3.5% by weight, preferably from about 0.10 to about 3.00%, more preferably from about 0.15 to about 2.50% by weight, particularly preferably from about 0.20 to about 2.25% by weight and especially preferably from about 0.25 to about 2.00% by weight of at least one alum, preferably a potassium, sodium, ammonium or guanidinium alum.

The properties of the hair and/or the scalp can still be better maintained despite dyeing and/or bleaching or can be protected against damage such as roughness, split ends and/or hair breakage when the method as contemplated herein is carried out with cosmetic pretreatment agents which additionally contain at least one silicone.

In a fifth particularly preferred embodiment, a method as contemplated herein is accordingly characterized in that the cosmetic composition in step i., based on its own weight, additionally contains from about 0.001 to about 5.00% by weight, of at least one silicone.

Silicones have excellent conditioning properties on the hair. In particular, they bring about better combability of the hair in wet and dry condition and in many cases have a positive effect on the hair grip and the softness of the hair.

Suitable silicones which can be used in the cosmetic compositions in step i. of the process as contemplated herein are preferably selected from:
(i) polyalkylsiloxanes, polyarylsiloxanes, polyalkylarylsiloxanes which are volatile or non-volatile, straight-chain, branched or cyclic, cross-linked or non-cross-linked;
(ii) polysiloxanes which contain in their general structure one or more organofunctional groups selected from:
  a) substituted or unsubstituted aminated groups;
  b) (per)fluorinated groups;
  c) thiol groups;
  d) carboxylate groups;
  e) hydroxylated groups;
  f) alkoxylated groups;
  g) acyloxyalkyl groups;
  h) amphoteric groups;
  i) bisulfite groups;
  j) hydroxyacylamino groups;
  k) carboxy groups;
  l) sulfonic acid groups; and
  m) sulfate or thiosulfate groups;
(iii) linear polysiloxane(A) polyoxyalkylene(B) block copolymers of type $(A-B)_n$, with n>3;
(iv) grafted silicone polymers having a non-silicone-containing organic basic structure which consists of an organic main chain which is formed of organic monomers which do not contain a silicone, on which least one polysiloxane macromer was grafted in the chain and optionally at least one chain end;
(v) grafted silicone polymers having a polysiloxane basic structure was grafted onto the non-silicone containing organic monomers, which have a polysiloxane main chain onto which at least one organic macromer that contains no silicone has been grafted in the chain and optionally at least one of its ends;
(vi) or mixtures thereof.

However, the use of specific polyorganosiloxanes (which are described in the following) in the cosmetic compositions of the method as contemplated herein leads to a particularly good color retention. Moreover, the aforementioned use enhances the suppleness and softness of the keratin fibers after dyeing and/or bleaching without causing an undesirable weighting of the fibers.

Particularly suitable are polyorganosiloxanes of the formula (1)

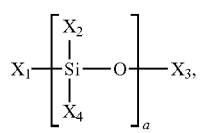 (I)

wherein
$X_1$ and $X_2$, independently of one another, mean OH, $OR^1$, $R^2$, O-PDMS or O-fsiloxane,
$X_3$ means hydrogen or a monovalent hydrocarbon radical having 1 to 8 carbon atoms per radical, PDMS or fsiloxane,
$X_4$ is a radical of the formula

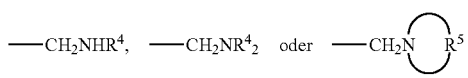

and
a is a number from 1 to 100, preferably a number from 1 to 5, wherein
$R^1$ means an alkyl radical having 1 to 8 carbon atoms,
$R^2$ means a monovalent, saturated or unsaturated hydrocarbon radical having 1 to 200 carbon atoms per radical, optionally substituted by the elements N, P, S, O, Si and halogen, PDMS stands for

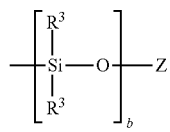

fsiloxane stands for

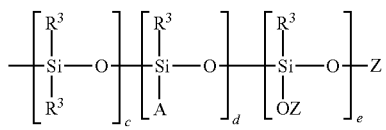

$R^3$ means, independently of one another, a monovalent, saturated or unsaturated hydrocarbon radical with 1 to 200 carbon atoms per radical which is optionally substituted by the elements N, P, S, O, Si and halogen,
A is a radical of the formula $R^6$—[$NR^7$—$R^8$—]$_f NR^7_2$, wherein
$R^6$ means a divalent linear or branched hydrocarbon radical having 3 to 18 carbon atoms,
$R^7$ means a hydrogen atom, an alkyl radical having 1 to 8 carbon atoms or an acyl radical,
$R^8$ means a divalent hydrocarbon radical having 1 to 6 carbon atoms,
b is a number from 1 to 2000, preferably from 1 to 1000,
c is 0 or a number from 1 to 2000, preferably from 50 to 1000,
d is a number from 1 to 1000, preferably from 1 to 10,
e is 0 or a number from 1 to 5,
f is 0, 1, 2, 3 or 4,
Z means hydrogen, an alkyl radical having 1 to 8 carbon atoms or

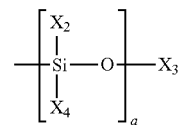

$R^4$ means a monovalent hydrocarbon radical having 1 to 18 carbon atoms and optionally N and/or O atoms, and
$R^5$ means a divalent hydrocarbon radical having 3 to 12 carbon atoms and optionally N and/or O atoms.

Examples of an alkyl radical $R^1$ are methyl, ethyl, n-propyl, isopropyl, 1-n-butyl, 2-n-butyl, isobutyl, tert-butyl, n-pentyl-, iso-pentyl, neo-pentyl, tert-pentyl, n-hexyl, n-heptyl, n-octyl, iso-octyl or 2,2,4-trimethylpentyl, wherein methyl, ethyl and butyl are preferred.

Examples of hydrocarbon radicals $R^2$ and $R^3$ are alkyl radicals such as methyl, ethyl, n-propyl, isopropyl, 1-n-butyl, 2-n-butyl, iso-butyl, tert-butyl, n-pentyl, iso-pentyl, neo-pentyl, tert=-pentyl, n-hexyl, n-heptyl, n-octyl, iso-octyl, 2,2,4-trimethylpentyl, n-nonyl, n-decyl, n-dodecyl, n-octadecyl, cyclopentyl, cyclohexyl, cycloheptyl, methylcyclohexyl, vinyl, 5-hexenyl, cyclohexenyl, 1-propenyl, allyl, 4-pentenyl, phenyl, naphthyl, anthryl, phenanthryl, o-tolyl, m-tolyl, p-tolyl, xylyl, ethylphenyl, benzyl, alpha-phenylethyl and beta-phenylethyl radicals. The methyl, ethyl, octyl and phenyl radical are preferred as $R^2$, the methyl and ethyl radicals are particularly preferred.

Examples of halogenated radicals $R^2$ and $R^3$ are the 3,3,3-trifluoro-n-propyl, 2,2,2',2',2'-hexafluoroisopropyl, heptafluoroisopropyl, o-chlorophenyl, m-chlorophenyl and p-chlorophenyl radical.

Examples of $R^4$ are the alkyl, cycloalkyl, aryl, alkaryl and aralkyl radicals listed for the hydrocarbon radicals $R^2$ and $R^3$.

Preferred examples of $R^5$ are radicals of the formulas —$CH_2$—$CH_2$—O—$CH_2$—$CH_2$—, —$CH_2$—$CH_2$—NH—$CH_2$—$CH_2$— or —$CH_2$—$CH_2$—NH—$CH_2$—, where the radical is —$CH_2$—O—$CH_2$—$CH_2$— is particularly preferred.

Examples of $R^6$ are alkylene radicals having 3 to 10 carbon atoms, such as propylene, butylene, pentylene, hexylene, heptylene, octylene, nonylene and decylene.

$R^7$ can be a hydrogen atom, a methyl, ethyl, n-propyl, iso-propyl, 1-n-butyl, 2-n-butyl, iso-butyl, tert-butyl, n-pentyl, iso-pentyl, neo-pentyl, tert-pentyl, n-hexyl, n-heptyl, n-octyl, iso-octyl, 2,2,4-trimethylpentyl or acetyl radical.

Preferred examples of $R^8$ are alkylene radicals such as methylene, ethylene, propylene, butylene, pentylene, or hexylene.

Z is preferably hydrogen or methyl, ethyl, n-propyl, iso-propyl, 1-n-butyl, 2-n-butyl, isobutyl, tert-butyl, n-pentyl, iso-pentyl, neo-pentyl, tert-pentyl, n-hexyl, n-heptyl, n-octyl, iso-octyl or 2,2,4-trimethylpentyl, wherein hydrogen, methyl, ethyl and butyl are particularly preferred.

Preferred radicals $X_4$ are corresponding to the above definitions of $R^4$ and $R^5$ aminomethyl, methylaminomethyl, dimethylaminomethyl, diethylaminomethyl, dibutylaminomethyl, cyclohexylaminomethyl, morpholinomethyl, piperidinomethyl, piperazinomethyl, ((diethoxymethylmethyl) cyclohexylaminomethyl, ((triethoxysilyl)methyl) cyclohexylaminomethyl, anilinomethyl, 3-dimethylaminopropylaminomethyl, bis(3-dimethylaminopropyl) aminomethyl radical and mixtures thereof. It is highly preferred when the hair treatment agent contains polyorganosiloxanes of the formula (I), which contain morpholinomethyl radical as the radical $X_4$.

According to definitions for $R^6$, $R^7$ and $R^8$, preferred examples of the radical A are:
—$(CH_2)_3NH_2$
—$(CH_2)_3$—NH—$(CH_2)_2$—$NH_2$
—$CH_2CH(CH_3)CH_2$—NH—$(CH_2)_2$—$NH_2$
—$(CH_2)_3$—NH(cyclohexyl)
—$(CH_2)_3$—$NHCH_3$
—$(CH_2)_3$—$N(CH_3)_2$
—$(CH_2)_3$—$NHCH_2CH_3$
—$(CH_2)_3$—$N(CH_2CH_3)_2$
—$(CH_2)4$-$NH_2$
—$CH_2CH(CH_3)CH_2$—$NH_2$
—$(CH_2)_3$—NH—$(CH_2)_2$—$NHCH_3$
—$(CH_2)_3$—NH—$(CH_2)_2$—$N(CH_3)_2$
—$(CH_2)_3$—NH—$(CH_2)_2$—$NHCH_2CH_3$
—$(CH_2)_3$—NH—$(CH_2)_2$—$N(CH_2CH_3)_2$
—$(CH_2)_3$[—NH—$CH_2CH_2]_2$—$NH_2$
—$(CH_2)_3$—NH(acetyl)
—$(CH_2)_3$—NH—$(CH_2)_2$—NH(acetyl) and
—$(CH_2)_3$—N(acetyl)-$(CH_2)_2$—NH(acetyl).

For manufacturing the polyorganosiloxanes of the formula (I), preferably implemented are commercially available polydimethylsiloxanes having terminal silanol groups and/or polydimethylsiloxanes with terminal alkoxy and silanol groups and/or amine-functionalized siloxanes which contain silanol groups or alkoxy and silanol groups with a dialkoxy and/or trialkoxysilane, which has a radical formula

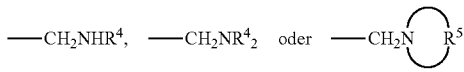

Correspondingly, in the formula (I) "fsiloxane" stands for a radical that is derived from an amine-functionalized siloxane.

Trialkoxysilanes or a mixture of dialkoxy and trialkoxysilanes are particularly preferably used, wherein the use of trialkoxysilanes alone are particularly preferred. When using trialkoxysilanes or a mixture of dialkoxy and trialkoxysilanes, at least partially cross-linked polyorganopolysiloxanes are obtained, independently of the structure of the siloxanes used and the position of the alkoxy and/or silanol groups in the siloxanes. In a very particularly preferred embodiment, the cosmetic agent contains cross-linked polyorganosiloxanes. In a highly preferred embodiment, the cosmetic composition contains cross-linked polyorganosiloxanes which have resulted from the conversion of siloxanes and trialkoxysilanes.

Preferred examples of the dialkoxy or trialkoxysilanes used include:
diethylaminomethylmethyldimethoxysilan,
dibutylaminomethyltriethoxysilan,
dibutylaminomethyltributoxysilan,
cyclohexylaminomethyltrimethoxysilane,
cyclohexylaminomethyltriethoxysilane,
cyclohexylaminomethyl-methyldiethoxysilane,
anilinomethyltriethoxysilan,
anilinomethylmethyldiethoxysilan,
morpholinomethyltriethoxysilan,
morpholinomethyltrimethoxysilan,
morpholinomethyltriisopropoxysilan,
3-dimethylaminopropyl-aminomethyltrimethoxysilane,
morpholinomethyltributoxysilane,
morpholinomethyltrialkoxysilane, wherein the alkoxy radical is a C1-C4-alkoxy radical,
especially a mixture of methoxy and ethoxy radical,
piperazinomethyltriethoxysilan,
piperidinomethyltriethoxysilane and
part of hydrolyzates thereof.

A particularly preferred silane is morpholinomethyltriethoxysilane.

A particularly preferred usable amine-functionalized siloxane is a copolymer of 3-(2-aminoethylamino)propylmethylsiloxy and dimethylsiloxy units which have silanol groups or alkoxy and silanol groups.

Identical or different siloxanes and identical or different silanes can be used In the preparation of the polyorganosiloxanes of the formula (I).

An especially preferred polyorganosiloxane is, for example, known under the INCI name Amodimethicone/Morphohnomethyl Silsesquioxane Copolymer and/or under the CAS number 1293390-78-9. This polyorganosiloxane is commercially available under the name Belsil® ADM 8301 E (ex Wacker). The raw material is a microemulsion and has the following ingredients: Amodimethicones/Morpholinomethyl Silsesquioxane Copolymer, trideceth-5, glycerol, phenoxyethanol and water.

The above-described polyorganosiloxanes are preferably used as aqueous suspensions or aqueous emulsions of polyorganosiloxanes. The dispersions may contain one or more surfactants as dispersants. The surfactants may be of any type, ionic and/or nonionic. Alternatively, inorganic solids such as silicas and/or bentonites may be used as dispersants. The mean particle size of the polyorganosiloxanes measured by employing light scattering in the dispersions is preferably in the range from about 0.001 to about 100 μm, more preferably from about 0.002 to about 10 μm. The pH values can vary from about 1 to about 14. The pH is preferably from about 3 to about 9, particularly preferably from about 5 to about 8.

Within the fifth preferred embodiment, a method as contemplated herein is particularly preferred in which at least one compound known under the INCI name Amodimethicone/Morpholinomethyl Silsesquioxane Copolymer is used as the silicone.

The pretreatment agent which is applied in method step i. of the method as contemplated herein can be made up as a low-viscous water-based emulsion, as a spray, as a cream, gel, lotion, paste, shampoo or conditioner.

The method as contemplated herein comprises the application of the pretreatment agent to ceramic fibers and an oxidative dyeing and/or bleaching treatment during a period of from about 5 seconds to about 24 hours following it.

A great advantage of the pretreatment agents used in step i. is that they are not only effective when applied immediately before the oxidative dyeing treatment, but can be applied up to about 24 hours beforehand, without fear of washing out the effect from external influences. In this way, it is possible, for example, to carry out step i. of the method as contemplated herein in the morning after the hair washing, and to carry out the oxidative dyeing treatment only in the evening.

Preferred methods as contemplated herein are characterized in that the period between method steps i. and ii. of from about 5 seconds to about 2.0 minutes, preferably from about 30 seconds to about 10 minutes, particularly preferably from about 1 to about 5 minutes.

Further preferred methods as contemplated herein are characterized in that the pretreatment agent applied in method step i. is allowed to act on the hair for a period of from about 5 seconds to about 120 minutes, preferably from about 10 seconds to about 10 minutes, before the method step ii. is started.

Further preferred methods as contemplated herein are characterized in that the pretreatment agent applied in method step i. is allowed to act on the hair for a period of from about 5 seconds to about 120 minutes, preferably from about 10 seconds to about 10 minutes, before step ii. takes place.

In a further preferred embodiment, the method as contemplated herein is characterized in that step ii, comprises applying a hair dyeing agent which preferably contains at least one oxidation dye precursor of the developer type and at least one oxidation dye precursor of the coupler type and at least one oxidizing agent.

Preferred oxidizing agents are selected from peroxo compounds, preferably selected from hydrogen peroxide, solid addition compound of hydrogen peroxide to inorganic or organic compounds, for example sodium perborate, sodium percarbonate, magnesium percarbonate, sodium percarbamide, polyvinylpyrrolidone n $H_2O_2$ (n is a positive integer greater than 0), urea peroxide and melamine peroxide, further selected from diammonium peroxodisulfate (also referred to as ammonium persulfate), disodium peroxodisulfate (also referred to as sodium persulfate) and dipotassium peroxodisulfate (also referred to as potassium persulfate), and mixtures of these oxidizing agents. Very particularly preferred oxidizing agents as contemplated herein are aqueous hydrogen peroxide solutions. The concentration of a hydrogen peroxide solution is, on the one hand, determined by the legal requirements and, on the other hand, by the desired effect; preferably from about 6 to about 12 weight percent solutions are used in water.

Preferred methods as contemplated herein are characterized in that the hair dyeing agents used in step ii., based on their weight, contain from about 0.5 to about 12% by weight, preferably from about 2 to about 10% by weight, particularly preferably from about 3 to about 6% by weight, of hydrogen peroxide (calculated as 100% strength $H_2O_2$).

Oxidative dyeing methods on keratin fibers usually proceed in an alkaline environment. In order to protect the keratin fibers as well as the skin as much as possible, however, the setting of a too high pH value is not desirable. Therefore, it is preferable that the pH of the hair dyeing agent used in step ii. is in the range of about 7 and about 11, especially in the range of about 8 and about 10.5, The pH values for the purposes of the present disclosure were pH values measured at a temperature of 22° C.

The alkalizing agents which can be used for setting the preferred pH value can be selected from the group ammonia, basic amino acids, alkali hydroxides, alkanolamines, alkali metal metasilicates, alkali phosphates and alkali metal hydrogenphosphates. Lithium, sodium, potassium, especially sodium or potassium, are preferably used as alkali metal ions. The basic amino acids which can be used as alkalizing agents are preferably selected from the group consisting of L-arginine, D-arginine, D,L-arginine, L-lysine, D-lysine, D,L-lysine, particularly preferably L-arginine, D-arginine, D,L-arginine used as an alkalizing agent as contemplated herein.

The alkali metal hydroxides which can be used as alkalizing agents are preferably selected from sodium hydroxide and potassium hydroxide.

The alkanolamines which can be used as alkalizing agents are preferably selected from primary amines having a C2-C6-alkyl basic body which carries at least one hydroxyl group. Particularly preferred alkanolamines are selected from the group the is formed from 2-aminoethane1-ol (monoethanolamine), 3-aminopropan-1-ol, 4-aminobutan-1-ol, 5-aminopentan-1-ol, 1-aminopropane-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol. Alkanolamines particularly preferred as contemplated herein are selected from the group of 2-aminoethan-1-ol, 2-amino-2-methylpropan-1-ol and 2-amino-2-methylpropane-1,3-diol.

For a dyeing which requires a strong brightening of very dark hair, the use of hydrogen peroxide or its addition products to organic or inorganic compounds is often not sufficient. In these cases, a combination of hydrogen peroxide and peroxydisulfate salts (persulfate salts) is generally used. Preferred persulfate salts are ammonium peroxydisulfate, potassium peroxydisulfate, sodium peroxydisulfate, as well as mixtures thereof.

The at least one persulphate salt is preferably contained in a total amount of from about 0.1 to about 25% by weight, particularly preferably in a total amount of from about 1 to about 15% by weight, based on the weight of the ready-to-use coloring agent.

Due to their reaction behavior, oxidation dye precursors can be classified into two categories, so-called developer components and coupler components. Coupling components do not form a significant dyeing in the context of the oxidative dyeing alone, but always require the presence of developer components. Developer components can themselves form the actual dye. The developer and coupler components are usually used in free form. In the case of substances having amino groups, however, it may be preferred to use them in salt form, especially in the form of the hydrochlorides or hydrobromides or of the sulfates.

Surprisingly, it was found that hair dyeings with particularly high fastness to washing could be achieved by the method as contemplated herein using at least one oxidation dye precursor of the developer type and at least one oxidation dye precursor of the coupler type. A particularly good improvement in fastness to washing was observed for formulations with the developer/coupler combination 1-hydroxyethyl-4,5-diaminopyrazol/3-aminophenol. Also the reduction of the hair damage was surprisingly high.

Particularly preferred developer components are selected from at least one compound from the group formed from p-phenylenediamine, p-toluenediamine, 2-(2-hydroxyethyl)-p-phenylenediamine, 2-(1,2-dihydroxyethyp-p-phenylenediamine, N,N-bis(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-propan-2-ol, bis(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis (2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl) phenol, 4,5-diamino-1-(2-hydroxyethyl) pyrazole, 2,4,5,6-tetraaminopyrimidine, 4-hydroxy-2,5,6-triaminopyrimidine, 2-hydroxy-4,5,6-triaminopyrimidine, the physiologically compatible salts of these compounds, and mixtures of these developer components and developer component salts.

Very particularly preferred developer components are selected from 4,5-diamino-1-(2-hydroxyethyl)pyrazole, p-toluenediamine, 2-(2-hydroxyethyl)-p-phenylenediamine, 2-methoxymethyl-p-phenylenediamine, N-(4-amino-3-methylphenyl)-N[3-(1H-imidazol-1-propyl)]amine, and mixtures of these compounds and their physiologically compatible salts. Extraordinarily preferred is 4,5-diamino-1-(2-hydroxyethyl)pyrazole and its physiologically compatible salts.

The developer components are preferably used in a total amount of from about 0.005 to about 10% by weight, particularly preferably from about 0.1 to about 5% by weight, respectively based on the weight of the ready-to-use dye.

For the purposes of this application, the term "ready-to-use coloring agent" is understood as meaning the mixture of all oxidation dye precursors and all oxidizing agents, optionally in combination with a suitable cosmetic carrier, for example, a cream base, and optionally in combination with at least one direct-acting dye.

Coupler components as contemplated herein permit at least one substitution of a chemical radical of the coupler by the oxidized form of the developer component. A covalent bond is thereby formed between the coupler and the developer component. Couplers are preferably cyclic compounds which carry at least two groups on the cycle, selected from (i) optionally substituted amino groups and/or (ii) hydroxyl groups. When the cyclic compound is a six-membered ring (preferably aromatic), the said groups are preferably in the ortho-position or meta-position.

Preferred methods as contemplated herein are characterized in that the at least one oxidation dye precursor of the coupler type is selected from one of the following classes:
3-aminophenol (m-aminophenol) and/or its derivatives,
3-aminoaniline (m-diaminobenzene) and/or its derivatives,
2-aminoaniline 1,2-diaminobenzene; o-diaminobenzene) and/or its derivatives,
2-aminophenol (m-aminophenol) and/or its derivatives,
naphthalene derivatives having at least one hydroxy group,
di- or trihydroxybenzene and/or its derivatives,
pyridine derivatives,
pyrimidine derivatives,
monohydroxyindole derivatives and/or monoaminoindole derivatives,
monohydroxyindoline derivatives and/or monoaminoindoline derivatives,
pyrazolone derivatives, for example 1-phenyl-3-methyl-pyrazol-5-on,
morpholine derivatives such as, for example, 6-hydroxybenzomorpholie or 6-aminobenzomorpholine,
quinoxaline derivatives such as, for example, 6-methyl-1,2,3,4-tetrahydroquinoxaline, Mixtures of two or more compounds from one or more of these classes are also preferred as contemplated herein within the scope of this embodiment.

Particularly preferred additional coupler components as contemplated herein are selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-di-chloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2'-hydroxyethylamino)benzene (=2-amino-4-hydroxyethylaminoanisole), 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino) ethanol, 2-[3-morpholine-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazole-5-on, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically compatible salts of the compounds named above. Very particularly preferred are 3-aminophenol, resorcinol, 2-methylresorcinol, 5-amino-2-methylphenol, 2-(2,4-diaminophenoxy) ethanol, 1,3-bis (2,4-diaminophenoxy)propane, 1-methoxy-2-amino-4-(2'-hydroxyethylamino) benzene, 2-amino-3-hydroxypyridine and 1-naphthol and their physiologically acceptable salts and mixtures of the components named.

The at least one coupler component is preferably used in a total amount of from about 0.005 to about 20% by weight, preferably from about 0.1 to about 5% by weight, respectively based on the weight of the application-specific oxidation coloring agent.

As contemplated herein, the following combinations of oxidation dye precursors of the developer type and of the coupler type are particularly preferred, wherein the amine compounds and the nitrogen heterocycles also may be present in the form of their physiologically compatible salts:
p-toluenediamine/resorcinol;
p-toluenediamine/2-methylresorcinol;
p-toluenediamine/5-amino-2-methylphenol;
p-toluenediamine/3-aminophenol;
p-toluenediamine/2-(2,4-diaminophenoxy)ethanol;
p-toluenediamine/1,3-bis(2,4-diaminophenoxy)propane;
p-toluenediamine/1-methoxy-2-amino-4-(2-hydroxyethylamino)benzene;
p-toluenediamine/2-amino-3-hydroxypyridine;
p-toluenediamine/1-naphthol;
2-(2-hydroxyethyl)-p-phenylenediamine/resorcinol;
2-(2-hydroxyethyl)-p-phenylenediamine/2-methylresorcinol;
2-(2-hydroxyethyl)-p-phenylenediamine/5-amino-2-methylphenol; 2-(2-hydroxyethyl)-p-phenylenediamine/3-aminophenol;
2-(2-hydroxyethyl)-p-phenylenediamine/2-(2,4-diaminophenoxy)ethanol;
2-(2-hydroxyethyl)-p-phenylenediamine/1,3-bis(2,4-daminophenoxy)propane;
2-(2-hydroxyethyl)-p-phenyl enediamine/1-methoxy-2-amino-4-(2-hydroxyethylamino)benzene;
2-(2-hydroxyethyl)-p-phenylenediamine/2-amino-3-hydroxypyridine;
2-(2-hydroxyethyl)-p-phenylenediamine/1-naphthol;
2-methoxymethyl-p-phenylenediamine/resorcinol;
2-methoxymethyl-p-phenylenediamine/2-methylresorcinol;
2-methoxymethyl-p-phenylenediamine/5-amino-2-methylphenol;
2-methoxymethyl-p-phenylenediamine/3-aminophenol;
2-methoxymethyl-p-phenylenediamine/2-(2,4-diaminophenoxy)ethanol;
2-methoxymethyl-p-phenylenediamine/1,3-bis(2,4-diaminophenoxy)propane;
2-methoxymethyl-p-phenylenediamine/1-methoxy-2-amino-4-(2-hydroxyethylamino)benzene;

2-methoxymethyl-p-phenylenediamine/2-amino-3-hydroxypyridine;
2-methoxymethyl-p-phenylenediamine/1-naphthol;
N-(4-amino-3-methylphenyl)-N-[3-(1H-imidazol-1-yl)propyl]amine/resorcinol;
N-(4-amino-3-methylphenyl)-N-[3-(1H-imidazol-1-yl)propy]/2-methylresorcinol;
N-(4-amino-3-methylphenyl)-N[3-(1H-imidazol-1-yl)propyl]amine/5-amino-2-methylphenol;
N-(4-amino-3-methylphenyl)-N-[3-(1H-imidazol-1-yl)propyl]amine/3-aminophenol;
N-(4-amino-3-methylphenyl)-N[3-(1H-imidazol-1-yl)propyl]amine/2-(2,4-diaminophenoxy)ethanol;
N-(4-amino-3-methylphenyl)-N[3-(1H-imidazol-1-yl)propyl]amine/1,3-bis(2,4-diaminophenoxy)propane;
N-(4-amino-3-methylphenyl)-N-[3-(1H-imidazol-1-yl)propyl]amine/1-methoxy-2-amino-4-(2-hydroxyethylamino)benzene;
N-(4-Amino-3-methylphenyl)-N-[3-(1H-imidazol-1-yl)propyl]amine/2-amino-3-hydroxypyridine;
N-(4-amino-3-methylphenyl)-N-[3-(1H-imidazol-1-yl)propyl]amine/1-naphthol;
4,5-diamino-1-(2-hydroxyethyl)pyrazole/resorcinol;
4,5-diamino-1-(2-hydroxyethyl)pyrazole/2-methylresorcinol;
4,5-diamino-1-(2-hydroxyethyl)pyrazole/5-amino-2-methylphenol;
4,5-diamino-1-(2-hydroxyethyl)pyrazole/3-aminophenol;
4,5-diamino-1-(2-hydroxyethyl)pyrazole/2-(2,4-diaminophenoxy)ethanol;
4,5-diamino-1-(2-hydroxyethyl)pyrazole/1,3-bis(2,4-diaminophenoxy)propane;
4,5-diamino-1-(2-hydroxyethyl)pyrazole/1-methoxy-2-amino-4-(2-hydroxyethylamino)benzene;
4,5-diamino-1-(2-hydroxyethyl)pyrazole/2-amino-3-hydroxypyridine;
4,5-diamino-1-(2-hydroxyethyl)pyrazole/1-naphthol.

Particularly preferred as contemplated herein are the combinations 4,5-diamino-1-(2-hydroxyethyl) pyrazole/3-aminophenol and p-toluenediamine/3-aminophenol. Extraordinarily preferred, particularly in view of the improvement in fastness against washing, is the combination 4,5-diamino-1-(2-hydroxyethyl)pyrazole/3-aminophenol.

In order to achieve a balanced and subtle nuance formation, it is preferred as contemplated herein if further coloring components are contained in the coloring agent which is used in step ii. of the method as contemplated herein.

In a further embodiment, the compounds described in step ii. of this variant of the method as contemplated herein additionally contain at least one direct-acting dye. These are dyes which are directly applied to the hair and do not require an oxidative process to form the color. Direct-acting dyes are usually nitrophenylenediamines, nitroaminophenols, azo dyes, anthraquinones or indophenols.

A further preferred method as contemplated herein is characterized in that coloring agent applied in step ii. is rinsed from the keratin fibers after a time of about 5-60 minutes, preferably about 30-45 minutes.

The method as contemplated herein in step ii. is preferably prepared from a two-component agent, wherein one component contains the oxidation dye precursors and the other components contain the oxidizing agent(s). The ready-to-use coloring agent for step ii. is then prepared by mixing both components directly before the application step ii. A separation into multicomponent systems is especially to be offered where incompatibilities of the ingredients are to be expected or feared.

A second object as contemplated herein is a cosmetic agent for the pretreatment of keratin fibers before a (preferably oxidative) dyeing and/or brightening, which is based on its weight, contains
a) from about 0.01 to about 4.00% by weight of at least one alum and
b) from about 0.001 to about 5% by weight of at least one silicone, and has a pH in the range from about 2.5 to about 5.

For preferred embodiments of the cosmetic agent as contemplated herein, especially with respect to preferred embodiments of the silicone and of the alum, the necessary changes having been made, is the same as that described for the method as contemplated herein.

In a first preferred embodiment, the cosmetic pretreatment agents of the second object as contemplated herein preferably contain from about 75.00 to about 99.98% by weight, more preferably from about 80.00 to about 99.50% by weight, particularly preferably from about 85.00 to about 99.00% by weight and especially from about 90.00 to about 98.50% by weight of water.

As contemplated herein, particularly preferred pretreatment agents of the second object as contemplated herein are characterized in that they contain as silicone at least one compound known under the INCI name Amodimethicone/Morpholinomethyl Silsesquioxane Copolymer in a total amount of from about 0.001 to about 5.00% by weight, preferably from about 0.005 to about 4.00% by weight, particularly preferably from about 0.01 to about 2.00% by weight, particularly preferably from about 0.02 to about 1.00% by weight, respectively based on the total weight of the pretreatment agent.

Particularly preferred cosmetic pretreatment agents of the second object as contemplated herein which, based on their weight, contain
a) from about 0.05 to about 3.5% by weight, preferably from about 0.10 to about 3.00% by weight, more preferably from about 0.15 to about 2.50% by weight, particularly preferably from about 0.20 to about 2.25% by weight and especially preferably from about 0.25 to about 2.00% by weight of at least one alum, preferably a potassium, sodium, ammonium or guanidinium alum, and
b) from about 0.001 to about 5.00% by weight, preferably from about 0.005 to about 4.00% by weight, particularly preferably from about 0.01 to about 2.00% by weight, very preferably from about 0.02 to about 1.00% by weight, at least one silicone known under the INCI name Amodimethicone/Morpholinomethyl Silsesquioxane copolymer, and
which have a pH in the range from about 3.0 to about 4.9, particularly preferably from about 3.5 to about 4.8, and especially preferably from about 4.0 to about 4.7.

It has been shown that the color protection and care action of the cosmetic pretreatment agent can be further improved if certain nonionic components are also contained in the pretreatment agents as contemplated herein. Moreover, these nonionic components have positive effects on the storage stability of the pretreatment agents as contemplated herein.

Nonionic components which are particularly suitable here are ethoxylates of decanol, undecanol, dodecanol, tridecanol, myristyl alcohol, cetyl alcohol and/or stearyl alcohol. Ethoxylated tridecanols have proven to be particularly suitable, which are incorporated with particular preference into the pretreatment agents as contemplated herein. Branched ethoxylated tridecanols are particularly preferred, especially branched tridecanols having 3 to 5 ethylene oxide units in the molecule.

Pretreatment agents particularly preferred as contemplated herein contain, respectively based on their weight, from about 0.001 to about 5% by weight, preferably from about 0.005 to about 3.5% by weight, particularly preferably from about 0.01 to about 2% by weight, further preferably from about 0.05 to about 1% by weight, and especially from about 0.1 to about 0.5% by weight, of branched, ethoxylated tridecanol, particularly preferably from about 0.001 to about 5% by weight, preferably from about 0.005 to about 3.5% by weight, particularly preferably from about 0.01 to about 2% by weight, further preferably from about 0.05 to about 1% by weight and especially from about 0.1 to about 0.5% by weight of branched, ethoxylated tridecanol having from about 3 to about 5 ethylene oxide units in the molecule.

Further surfactants and emulsifiers are preferably contained not at all or only in small amounts in the pretreatment agents as contemplated herein.

Preferred pretreatment agents as contemplated herein contain, based on the total weight of the agent, from about 0.001 to a maximum of about 6% by weight of surfactant(s), wherein the abovementioned ethoxylates of decanol, undecanol, dodecanol, tridecanol, myristyl alcohol, cetyl alcohol and/or stearyl alcohol are included.

The pretreatment agents as contemplated herein are preferably formulated in low viscosity, i.e., with a viscosity (measured at 20° C.) in the range from about 10 to about 2000 mPas, preferably from about 20 to about 1000 mPas, particularly preferably from about 50 to about 800 mPas. It has also been shown that thickening polymers can mitigate the effect as contemplated herein so that preferred pretreatment agents as contemplated herein are characterized in that they contain thickening polymers in a total amount of less than about 2.5% by weight, preferably less than about 1% by weight, more preferably less than about 0.5% by weight and especially less than about 0.01% by weight, respectively based on the weight of the pretreatment agent.

The pretreatment agents as contemplated herein can contain further ingredients. Polyhydric alcohols which have moisturizing properties are preferably used here. Preferred pretreatment agents as contemplated herein are those which contain at least one polyhydric alcohol, preferably selected from the group of sorbitol and/or glycerol and/or 1,2-propylene glycol or mixtures thereof, in a total amount of from about 0.05 to about 15% by weight, preferably from about 0.1 to about 10% by weight, particularly preferably from about 0.15 to about 5% by weight and especially from about 0.15 to about 1% by weight, respectively based on the weight of the pretreatment agent.

For certain fields of application, it may be advantageous to use only one of the three above-mentioned preferred polyhydric alcohols, Glycerin is preferred in most cases. However, mixtures of two of the three polyhydric alcohols or all three polyhydric alcohols may be preferred in other fields of application.

In addition to sorbitol, glycerol and 1,2-propylene glycol, suitable further polyhydric alcohols are those having at least 2 OH groups, preferably mannitol, xylitol, polyethylene glycol, polypropylene glycol and mixtures thereof. Among these compounds, those having 2 to 12 OH groups and especially those having 2, 3, 4, 5, 6 or 10 OH groups are preferred.

Poly hydroxy compounds having 2 OH groups are, for example, glycol ($CH_2(OH)CH_2OH$) and other 1,2-diols such as H—$(Cl_2)_n$—$CH(OH)CH_2OH$ with n=2, 3, 4, 5, 6, 7, 8, 9, 10, 11, 12, 13, 14, 15, 16, 17, 18, 19, 20. 1,3-diols such as H—H—$(CH_2)_n$—CH(OH) $CH_2CH_2OH$ with n=1, 2, 3, 4, 5, 6, 7, 8, 9, 10, 11, 12, 13, 15, 16, 17, 18, 19, 20 can also be used as contemplated herein. The (n,n+1)- or (n,n+2)-diols with non-terminal OH groups can also be used. Important representatives of polyhydroxy compounds having 2 groups are also the polyethylene and polypropylene glycols. For example, xylitol, propylene glycols, polyethylene glycols, especially those having average molecular weights of 200-800, can be used as preferred further polyhydric alcohols. The use of glycerol is particularly preferred, so that agents which contain no other polyhydric alcohols other than glycerol are particularly preferred.

The use of certain care products in the pretreatment compositions is preferred with regard to the pretreatment prior to oxidative dyeing and/or bleaching treatment.

Preferred pretreatment agents as contemplated herein are characterized in that they additionally contain a care substance or substances in a total amount of from about 0.001 to about 10% by weight, preferably from about 0.005 to about 7.5% by weight, particularly preferably from about 0.01 to about 5% by weight and especially from about 0.05 to about 2.5% by weight, respectively based on the total weight of the pretreatment agent. Preferred care product(s) are selected from at least one of the following named groups:
i. L-carnitine and/or its salts;
ii. Taurine and/or its salts;
iii. Niacinamide;
iv. Ubiquinone;
v. Ectoin;
vi. Vitamins and/or provitamins and/or vitamins derivatives;
vii. Flavonoids.

As a further ingredient, the pretreatment agents as contemplated herein can particularly preferably contain one or more amino acids.

As contemplated herein, particularly preferred amino acids are from the group of glycine, alanine, valine, leucine, isoleucine, phenylalanine, tyrosine, tryptophan, proline, aspartic acid, glutamic acid, asparagine, glutamine, serine, threonine, cysteine, methionine, lysine, arginine, histidine, 4-aminobutyric acid (GABA), betaine, L-cystine (L-Cyss), L-carnitine, L-citrulline, L-theanine, 3', 4'-dihydroxy-L-phenylalanine (L-Dopa), 5'-hydroxy-L-tryptophan, L-homocysteine, S-methyl-L-methionine, S-allyl-L-cysteine sulfoxide, L-trans-4-hydroxyproline, L-5-oxoproline (L-pyroglutatnic acid), L-phosphoserine, creatine, 3-methyl-L-histidine, L-ornithine, wherein both the individual amino acids and mixtures can be used.

Preferred pretreatment agents as contemplated herein contain one or more amino acids in narrower amount ranges. Here, pretreatment agents as contemplated herein are characterized in that they contain amino acid(s) from about 0.01 to about 5% by weight, preferably from about 0.02 to 2.5% by weight, particularly preferably from about 0.05 to about 1.5% by weight, more preferably from about 0.075 to about 1% by weight and especially from about 0.1 to about 0.25% by weight, as a care product, preferably from the group glycine and/or alanine and/or valine and/or lysine and/or leucine and/or threonine, respectively based on the total weight of the pretreatment agent.

A third object of the present disclosure is the use of a cosmetic agent, which, based on its weight, has
a) from about 0.01 to about 4.00% by weight of at least one alum and
b) from about 0.001 to about 5.00% by weight of at least one silicone, and has a pH in the range from about 2.5 to about 5, for color retention of dyed keratin fibers.

For preferred embodiments of the use as contemplated herein, the necessary changes having been made, applies to the said method as contemplated herein and to the said cosmetic agent as contemplated herein.

EXAMPLES

Hair strands were immersed for one minute in an aqueous composition containing
2.00% by weight of $KAl(SO_4)_2 \times 12\ H_2O$,
0.05% by weight Amodimethicone/Morpholinomethyl Silsesquioxane Copolymer,
optionally from about 0.001 to about 1.0% by weight of glycerin and/or from about 0.005% by weight to about 1.0% by weight, branched trideceth-5, and
water (ad 100).

Subsequently, the hair strands were dried, a freshly prepared dye-cream oxidation agent mixture was applied to the strands and left to act for 30 minutes. The coloring agent was then rinsed with water and the hair combed and, if necessary, dried.

The pretreatment as contemplated herein with aqueous compositions which contain at least one alum and at least one compound known under the INCI name Amodimethicone/Morpholinomethyl Silsesquioxane Copolymer was able to obtain an excellent color protection. In particular, the color fidelity of the coloration on the so-called b-axis in the lab color space (EN ISO 11664-4) was able to be strengthened (lower shift of the color in the direction yellow or blue).

In addition, the hair damage compared to an oxidative dyeing without pretreatment as contemplated herein was able to be significantly reduced. The sensory evaluation of the hair by trained hairdressers also proved that hair treated as contemplated herein had a softer and smoother feel after dyeing than untreated hair after dyeing.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for the color retention of dyed keratin fibers, the method comprising:
   i. applying a cosmetic composition to dyed keratin fibers as a pretreatment agent for keratin, and
   ii. subjecting the keratin fibers to a dyeing and/or brightening within a period of 5 seconds to 24 hours after to step i.,
   wherein the cosmetic composition has, based on its own weight, from 0.01 to 4.00% by weight of at least one alum and a pH value in the range of 2.5 to 5.

2. Method according to claim 1, further comprising subjecting the keratin fibers in step ii. to an oxidative dyeing.

3. Method according to claim 1, wherein the cosmetic composition comprises an alum of the formula $M^I Al(SO_4)_2 \times 12\ H_2O$, in which $M^I$ is a potassium, ammonium, or guanidinium ion.

4. Method according to claim 1, wherein the cosmetic composition, based on its own weight, comprises from 0.05 to 3.50% by weight of at least one potassium, sodium, ammonium and/or guanidinium alum.

5. Method according to claim 1, wherein the cosmetic composition has a pH value of from 3.0 to 4.9.

6. Method according to claim 1, wherein the cosmetic composition, based on its weight, additionally comprises from 0.001 to 5.00% by weight of at least one silicone.

7. Method according to claim 6, wherein at least one compound known under the INCI name Amodimethicone/Morpholinomethyl Silsesquioxane Copolymer is used as the silicone.

8. Cosmetic agent for the pretreatment of keratin fibers before a dyeing and/or brightening, wherein the cosmetic agent comprises, based on its weight:
   a) from 0.01 to 4.00% by weight of at least one alum; and
   b) from 0.001 to 5% by weight of at least one silicone;
   wherein the cosmetic agent has a pH in the range from 2.5 to 5.00.

9. Cosmetic agent according to claim 8, wherein it comprises, based on its weight, from 75.00 to 99.98% by weight of water.

10. Cosmetic agent according to claim 8, wherein the cosmetic agent is utilized for color retention of dyed keratin fibers.

11. Method according to claim 4, wherein the cosmetic composition, based on its own weight, comprises from 0.10 to 3.0% by weight of at least one potassium, sodium, ammonium and/or guanidinium alum.

12. Method according to claim 11, wherein the cosmetic composition, based on its own weight, comprises from 0.15 to 2.50% by weight of at least one potassium, sodium, ammonium and/or guanidinium alum.

13. Method according to claim 12, wherein the cosmetic composition, based on its own weight, comprises from 0.20 to 2.00% by weight of at least one potassium, sodium, ammonium and/or guanidinium alum.

14. Method according to claim 13, wherein the cosmetic composition, based on its own weight, comprises from 0.25 to 1.50% by weight of at least one potassium, sodium, ammonium and/or guanidinium alum.

15. Method according to claim 5, wherein the cosmetic composition has a pH value of from 3.5 to 4.8.

16. Method according to claim 15, wherein the cosmetic composition has a pH value of from 4.0 to 4.7.

17. Cosmetic agent according to claim 8, wherein at least one compound known under the INCI name Amodimethicone/Morpholinomethyl Silsesquioxane Copolymer is used as the silicone.

18. Cosmetic agent according to claim 8, wherein the cosmetic agent has a pH of from 3.5 to 4.8.

19. Cosmetic agent according to claim 8, wherein the cosmetic agent has a pH of from 4.0 to 4.7.

* * * * *